United States Patent [19]

Polaschegg et al.

[11] Patent Number: 5,540,265
[45] Date of Patent: Jul. 30, 1996

[54] CONTAINER FOR COLLECTION OF CONCENTRATE

[75] Inventors: Hans-Dietrich Polaschegg, Oberursel; Walter Pieper, Florstadt, both of Germany; Daniel Weber, Astoffort, France

[73] Assignee: Fresenius AG, Bad Homburg, Germany

[21] Appl. No.: 81,747

[22] Filed: Jun. 23, 1993

[30] Foreign Application Priority Data

Jun. 26, 1992 [DE] Germany .............................. 9217989 U
Feb. 5, 1993 [DE] Germany ........................... 43 03 372.5

[51] Int. Cl.[6] .......................... A61M 1/14; A61M 39/00
[52] U.S. Cl. ........................... 141/301; 141/67; 141/114; 141/324; 141/326; 141/346; 141/352; 604/416; 210/647; 251/149.6
[58] Field of Search ............................. 141/2, 9, 10, 18, 141/21, 67, 68, 91, 92, 100, 114, 285, 286, 313, 314, 324–326, 301, 357, 346–349, 351–354; 604/416; 222/105, 106, 395, 400.7; 285/131, 132, 133.1; 366/136, 137; 138/111, 114, 115; 210/646, 647; 137/268; 251/149.6

[56] References Cited

U.S. PATENT DOCUMENTS

| 1,101,574 | 6/1914 | Shephard | 141/324 X |
|---|---|---|---|
| 2,546,502 | 3/1951 | Harrington | 285/132 X |
| 3,563,267 | 2/1971 | Thompson | 251/149.6 X |
| 3,842,870 | 10/1974 | Burgess | 141/286 |
| 4,132,644 | 1/1979 | Kolberg | 210/85 |
| 4,195,672 | 4/1980 | Freeman | 141/91 |
| 4,360,996 | 11/1982 | Rutter | 141/10 X |
| 4,386,634 | 6/1983 | Stasz et al. | 141/2 |
| 4,617,012 | 10/1986 | Vaillancourt | 604/29 |
| 4,734,198 | 3/1988 | Harm et al. | 210/647 |
| 4,745,950 | 5/1988 | Mathieu | 251/149.6 X |
| 4,938,262 | 7/1990 | Williams et al. | 141/114 |
| 5,121,857 | 6/1992 | Hutchinson | 222/105 X |

FOREIGN PATENT DOCUMENTS

| 0198407 | 10/1986 | European Pat. Off. . |
|---|---|---|
| 0278100A2 | 12/1987 | European Pat. Off. . |
| 0443324A1 | 1/1991 | European Pat. Off. . |
| 3152050C2 | 8/1982 | Germany . |
| 3212230A1 | 1/1983 | Germany . |
| WO83/00812 | 3/1983 | Germany . |
| 8633262 | 2/1987 | Germany . |
| 8813659 | 12/1988 | Germany . |
| 91125693 | 3/1992 | Germany . |
| 9217989.4 | 6/1993 | Germany . |
| 9217989 | 6/1993 | Germany . |
| 3844174 | 5/1998 | Germany . |

*Primary Examiner*—J. Casimer Jacyna
*Attorney, Agent, or Firm*—Robbins, Berliner & Carson

[57] ABSTRACT

The invention concerns a bag to accommodate solid or fluid concentrate which is used to prepare dialysis fluid using a dialysis machine. The bag consists of a bag body and at least one opening, whereby the opening is sealingly surrounded by a plug component (220). In the coupled state with a second plug component (210), the plug component (220) forms a flow connection with the interior of the bag. The plug component also has coupling means (276, 278) which are suitable to be connected with a second complementary plug component (210), which is disposed on the dialysis machine. By means of the plug connector, in the coupled state, a first flow path is formed from the dialysis machine to the interior of the bag and a second flow path is formed back from the interior of the bag to the dialysis machine.

35 Claims, 8 Drawing Sheets

CONTAINER FOR COLLECTION OF CONCENTRATE

BACKGROUND OF THE INVENTION

The invention concerns a bag to accommodate solid or fluid concentrate for the preparation of dialysis fluid using a dialysis machine with a bag body and with at least one opening as well as a plug connector for use with such a bag.

Usually, with the hemodialysis machines used nowadays, the concentrates used for preparation of the dialysis fluid are prepared in the plant and transported to the user in canisters. Both the preparation and the transportation of such canisters filled with fluid concentrate are expensive, since in practice, it is primarily only water which is delivered from the manufacturer to the patient and, furthermore, the empty canisters represent an environmental problem. Particularly problematic is the storage and transportation of canisters filled with a bicarbonate concentrate since the canisters become swollen through the release of carbon dioxide gas and are thus under excess pressure. A bursting problem thus exists with such swollen containers in the event of improper handling of canisters.

Consequently, bedside systems have been proposed with which prepared dialysis fluids are made available or with which powdered concentrates, in particular bicarbonate concentrates, are mixed with water.

The first type system includes the long-known central dialysis fluid supply systems, which in particular provide dialysis fluid in circuits for a plurality of dialysis machines in the clinic.

On the other hand, powdered concentrates are also provided which are linked via a pipe system with the dialysis machine on one side and via a water line with a water source on the other. With such a system, fresh bicarbonate concentrate, which can be supplied directly to the dialysis machine without significant release of $CO_2$ gas, is made available on-line. Such a system is described, for example, in European patents A1-0,278,100 and A1-0,443,324.

Since such containers must frequently be exchanged, simple attachment and detachment of such containers using a connector system is advantageous. However, such a system is not described in the two European patents mentioned.

Furthermore, it is advantageous that a dialysis machine be capable of being connected with a variety of concentrate or dialysis fluid supply arrangements, for example, with a simple connector arrangement, the dialysis machine from a central supply unit can be connected to a bag containing bicarbonate powder.

An object of the invention is to provide a simple and safe arrangement for preparation of dialysis fluid from solid and/or fluid concentrate sources, whereby the transport volume of the concentrate is reduced to a minimum, using a dialysis machine.

A further object of the invention is to provide a plug connector with which the handling of this arrangement is easy and safe for different concentrate sources.

SUMMARY OF THE INVENTION

These and other objects are achieved by an arrangement for preparation of dialysis fluid from solid and/or fluid concentrate sources as described herein, advantageously including a plug connector as also described herein. The bag according to the invention usually consists of a flexible material, such as, for example, PVC, PVP, or polyethylene. A plug connector disposed directly in the body of the bag, i.e., in the wall of the bag replaces the formerly usual hose connection between the dialysis machine and the concentrate container. Thus, the duct paths are advantageously shortened. The bag is exchanged simply by means of the plug connector and fastened securely to the dialysis machine.

BRIEF DESCRIPTION OF THE DRAWINGS

In the following the invention is described with reference to exemplary embodiments in conjunction with the accompanying drawings, wherein.

DETAILED DESCRIPTION OF THE INVENTION

It must be considered a particular advantage of the bag according to the invention that the concentrate container is connected to the dialysis machine via a single connection, which enables water to flow in and diluted concentrate to be withdrawn.

Saturation of the water flowing in with concentrate which is to be diluted is favored if the fluid flowing in is conducted into the interior of the body of the bag through a tube. Preferably, the diluted concentrate is conducted to the dialysis machine via a tube projecting into the interior of the bag, which tube is provided with a filter on its suction end. The flow paths for the incoming and outgoing solution can be disposed in parallel or concentrically in the plug connector. With concentric disposition of the flow paths in the plug arrangement, it is advantageous if the inlet and the outlet are disposed in parallel on the bag-side plug component.

In a preferred embodiment, the bag according to the invention has coding on its plug component, which characterizes specific bag contents in each case. It is thus assured that the proper concentrate container is always connected to the proper fluid line of the dialysis machine. In order to prevent damage or contamination of the bag-side plug component during transportation, it is preferably covered by a locking cap until use.

The plug connector according to the invention is distinguished by a group of significant advantages. By means of the valve element shiftably incorporated into the valve chamber of the socket body, it is possible to provide for differing operating states of the plug connector. Thus, for example, the fluid feed channel and the discharge channel are short-circuited in the closed position of the second, device-side plug component since the movable valve element is pushed by the preloaded compression spring toward the input side of the second plug component, i.e., toward the side on which the first, bag-side plug component is attached. In contrast, when the bag is attached, the valve element is shifted away from the input side against the pressure of the spring. Thus, according to the invention, when the concentrate container is attached, the first and second flow paths are sealed off from each other through the disposition of sealing means.

In order to completely disinfect the second plug component before use of the concentrate container, a cleaning cap can be slipped onto the second, device-side plug component, which cap likewise pushes against the pressure of the spring from the input side. In the cleaning cap, the first and second flow paths are short-circuited such that complete cleaning and disinfection of the second plug component is assured.

According to another embodiment of the invention, the second plug component has an additional fluid inlet channel which can be connected to an additional concentrate container. However, this second inlet channel is linked with the valve chamber only when the movable valve element is in the closed position. When the bag has been attached, this second inlet channel is sealed off from the valve chamber by sealing means, which are attached to the valve element. It is thus assured that in each case, only one concentrate container is linked to the dialysis fluid circuit via the plug connector.

The socket thus makes it possible to design a universally usable dialysis machine, whereby extremely diverse feed systems can be connected by means of only a single plug connector. This results in reduced expenditures for apparatus. Moreover, it is very advantageous that only one socket, which must be cleaned and serviced, is present.

The plug connector according to the invention can be designed such that both the inlet and the outlet channel open respectively out of the wall of the body of the socket into the valve chamber, and that the flow paths, depending on the position of the movable valve element, are short-circuited or separated from each other. However, according to a second embodiment of the invention, a sealing liner can be introduced into the valve chamber, and the second plug component is then designed such that a channel extends through the socket body and the sealing liner and empties from an opening in the sealing liner into the valve chamber. Again, in this embodiment, the mere position of the valve element effects either the short-circuiting or the separation of the two flow paths.

The valve element can be produced in one piece with the shank element against which the compression spring rests. Alternatively, the valve element can be moved by a push rod linked to the shank.

With the sealing arrangement according to the invention it is possible very simply to engage the sealing means provided by shifting the valve element into the position determined in each case by the first, bag-side plug component such that with insertion of the bag-side plug component a switchover of the device-side plug component occurs automatically. When no bag is attached, the valve element is brought into the closed position by the elastic element, preferably a compression spring.

The sealing means comprise either at least two O-rings with an interval between them inserted in each case in a ring groove, or at least one movable O-ring, whereby the O-rings are engaged in each case with a cylindrical region of the valve element. With these sealing means, the device-side plug component is securely sealed in the closed position against the input side and, simultaneously, the two flow paths are effectively separated when the bag is attached.

Furthermore, it can be advantageous if the valve chamber, which extends between the end section of the device-side plug component opposing the input side and the valve element, is partitioned into two partial chambers against the elastic element by means of an elastic wall, whereby one partial chamber accommodates the elastic element and the intake of the fluid occurs in the other partial chamber. Thus, contamination of the elastic element or the fluid is prevented such that the cleaning of the coupling liner is substantially simplified. Via the plug arrangement according to the invention, the dialysis device can be connected not only with a bag with solid or fluid concentrate, but also can be linked, for example, with a central concentrate supply. Water or aqueous solutions can be used as solvents; however, in the following only water is mentioned.

The plug for connection to the central concentrate supply can be designed as a simple plug in the form of a tube since only one flow channel is required. The concentrate can however also be connected via the second feed line in the second plug component provided according to a preferred embodiment of the invention.

With a double-lumen concentrate plug, the water fed to the plug connector and the bag is first introduced into solid or fluid concentrate, e.g., bicarbonate powder, and the dissolved concentrate, e.g., saturated bicarbonate solution, is then fed back through the plug connector and forwarded to the dialysis machine. The tube line used, i.e., between the plug connector and the dialysis machine, can be designed concentrically, i.e., with an inner and an outer tube, or can comprise two parallel channels.

In the following different embodiments of a plug connector according to FIGS. 1 through 4 are described. The plug connector consists of a first and second plug component, whereby the first plug component is linked with the concentrate bag (bag-side plug component); the second plug component (device-side plug component or coupling socket) is disposed on the dialysis machine.

First, the plug connector has a device-side second plug component disposed on a dialysis machine, referred to in the following as a coupling socket, 10'. The coupling socket, 10' has a socket body, 12' which is provided with an essentially cylindric recess, 14' extending over part of the length of the socket body, 12'. According to the embodiment of FIG. 4, the socket body has different diameters in subregions.

Behind its free insertion end, 16' which faces the input side, the recess, 14' has a groove 18 which constitutes part of the catch means to lock a bag-side connector 20 in position—as explained below. Moreover, a sealing ring, 22' is advantageously provided inside the recess, 14' to seal the bag-side plug in the connected state against the surroundings.

Figure 4:
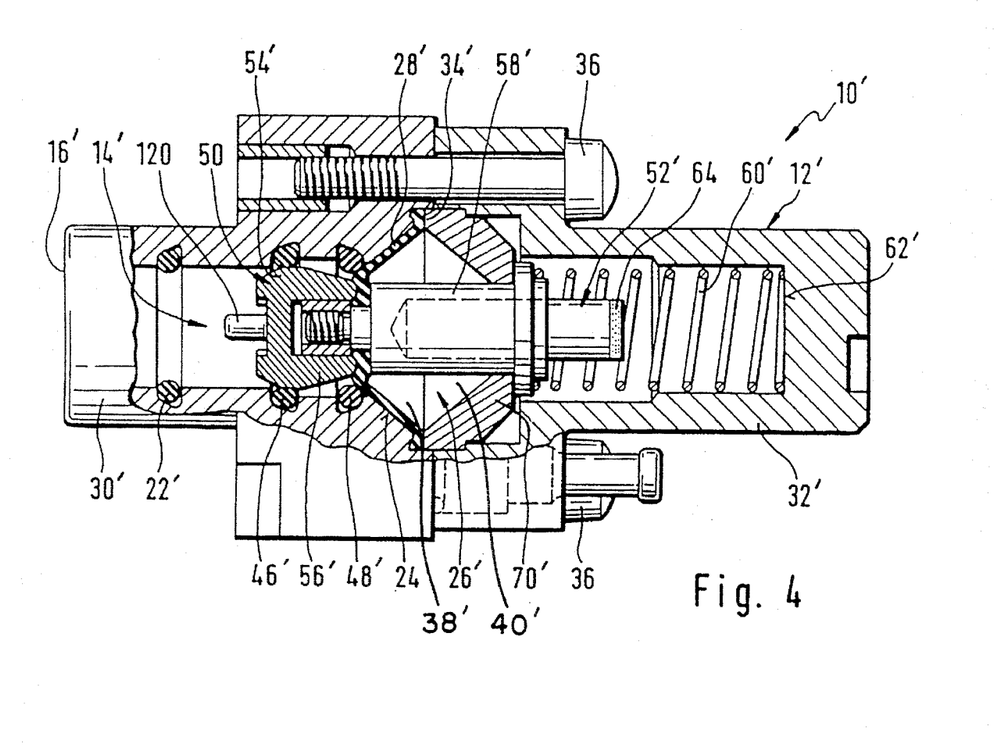
FIG. 4 is a side sectional view of another exemplary embodiment of the second plug component, wherein depiction of the inlet channel and the outlet channel is omitted.

In the central part 24 of the recess, 14' a valve chamber 26 with a relatively large diameter is provided, wherein an elastic wall, 28' is stretched perpendicular to the main axis of the socket body, 12'. For this, the socket body, 12' is divided into two socket parts, 30' and, 32' such that the wall, 28' can be stretched in the joint 34 by means of the bolts 36, as can be seen in FIG. 4. The wall, 28' thus divides the valve chamber, 26' into a left chamber half, 38' and a right chamber half, 40', which are variable in volume based on the shifting of the wall, 28'.

Figure 1:
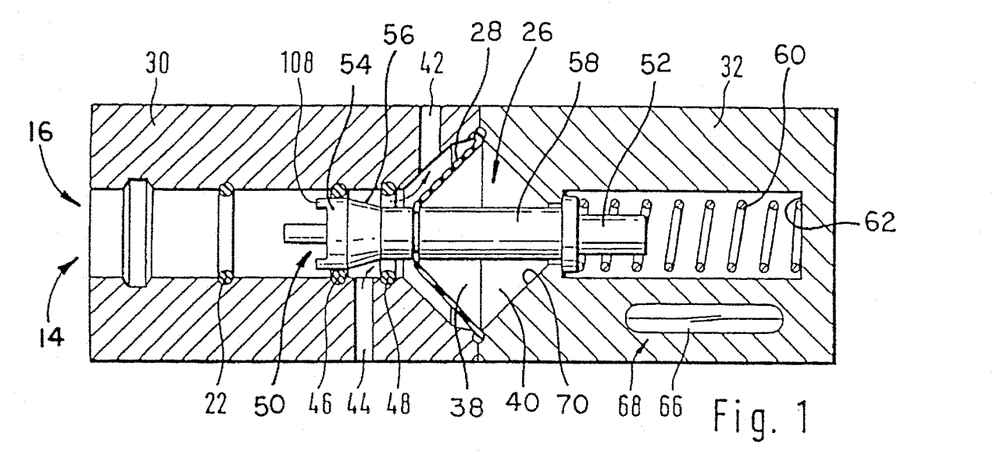
FIG. 1 is a schematic sectional view of an exemplary embodiment of the second plug component, wherein a closed position of the valve element is depicted.

An outlet channel 42, which can be linked with the dialysis fluid system of a dialysis machine (not shown), leaves the left chamber half 38 of the embodiment of FIG. 1. On the other side, this valve chamber half 38 has a flow connection via the cylindric recess 14 with an inlet channel 44, which opens into the recess 14 in the region 45 delimiting the valve chamber half 38.

As can be seen in FIGS. 1 through 4, on both sides of the inlet channel, 44', a ring-shaped sealing arrangement 46', 48' is provided in the form of an O-ring in each case.

Moreover, a valve element, 50' is provided in the recess, 14' which has a cylindric end region, 52' in the back, whereby the element, 50' and the end region, 52' are separated from each other by the flexible wall, 28'.

The valve element, 50' itself has an essentially cylindric front region, 54' and a conic region, 56' tapering toward the back. The conic region, 56' is joined by the shank, 58' forming the cylindric end region, 52' against the end of which an elastic element, 60' in the form of a spring rests, which spring is disposed in the end region, 62' of the recess, 14'. Attached to the end of the shank 58 is a magnet 64, which acts along with a reed switch 66 disposed on part 32, whereby the magnet 64 and the reed switch 66 form a sensor 68, with which the coupling process can be monitored.

FIG. 1 depicts an operating state in which no bag-side plug 20 is found in the recess 14. Thus, by means of the spring 60 the valve element 50 is preloaded farther toward the left than is possible with a stop 70 surrounding the shank 58, which is braced against the right chamber half 40. Thus, the cylindric front region 54 of the valve element 50 makes sealing contact with the left ring-shaped sealing arrangement 46, and thus locks the inlet channel 44 against the environment. This position is referred to as the closed position.

On the other side, because of the conic disposition of the conic region 56, a ring-shaped space is created in the region of the inlet channel 44 such that a flow connection to the outlet channel 42 is made through this ring-shaped space and the left valve chamber half 38. Thus, a flushing of the coupling socket 10 and also of the dialysis machine with water or disinfecting solution is possible.

Figure 2:
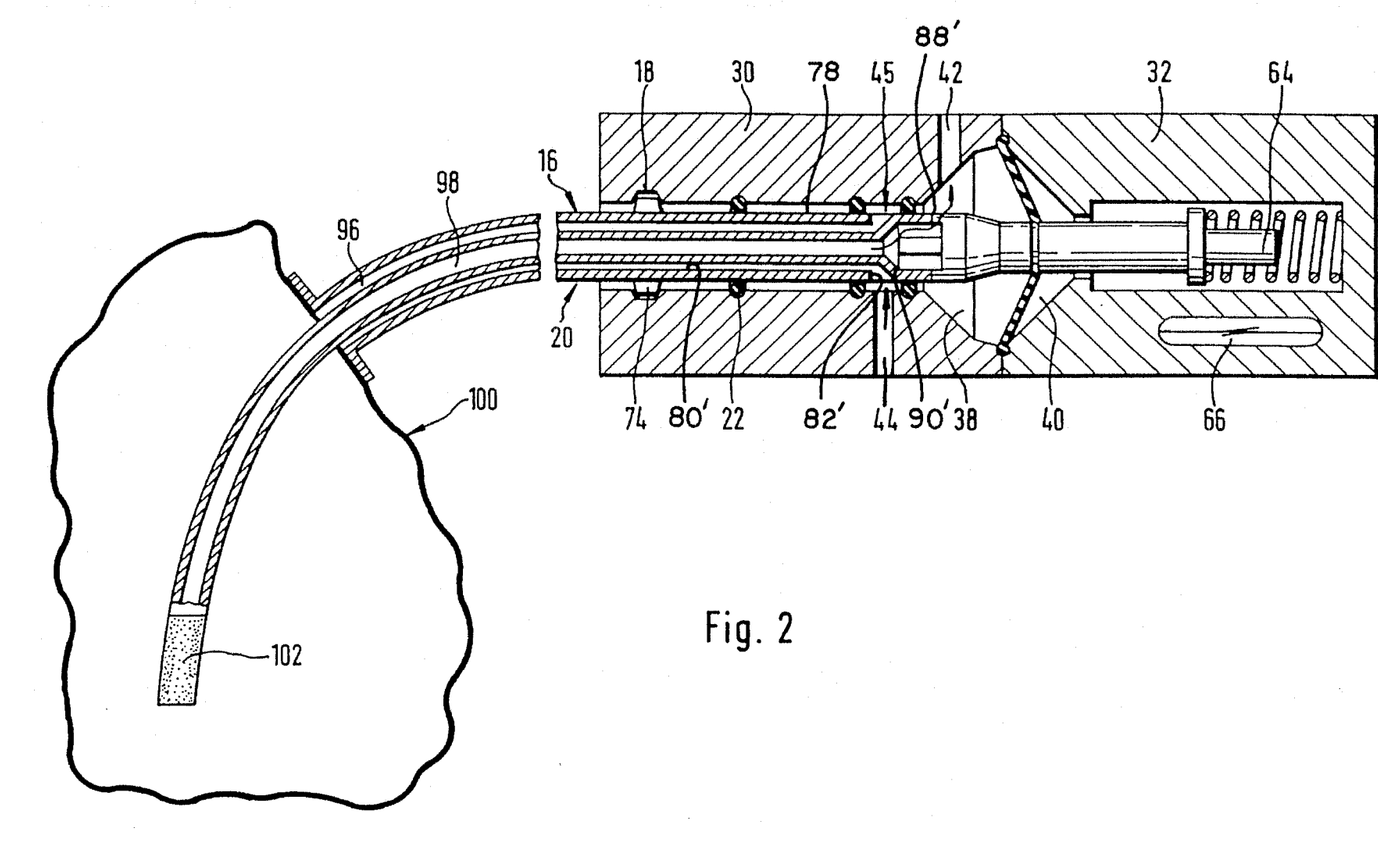
FIG. 2 is a side sectional view of the plug connector according to FIG. 1, wherein a double-lumen plug is connected to the connector of a bag filled with bicarbonate powder.

FIG. 2 depicts an operating state in which the bag-side plug 20 is inserted into the recess 14, whereby catch means 74, which are disposed on the plug 20, are engaged with the catch recess 18. According to a similar embodiment depicted in FIG. 5, the bag-side plug 72 is designed with a double lumen and comprises an inner tube 76 as well as an outer tube 78, which open into a back handle section 79 and between which a ring-shaped channel 80 is formed. This ring-shaped channel 80 has a front recess 82 penetrating the outer surface of the outer tube 78, which advantageously surrounds the end of the first plug component 72 facing the coupling socket 12 in the shape of a ring. In the handle section 79, the channel 80 opens into a first feed opening 84.

Figure 5:
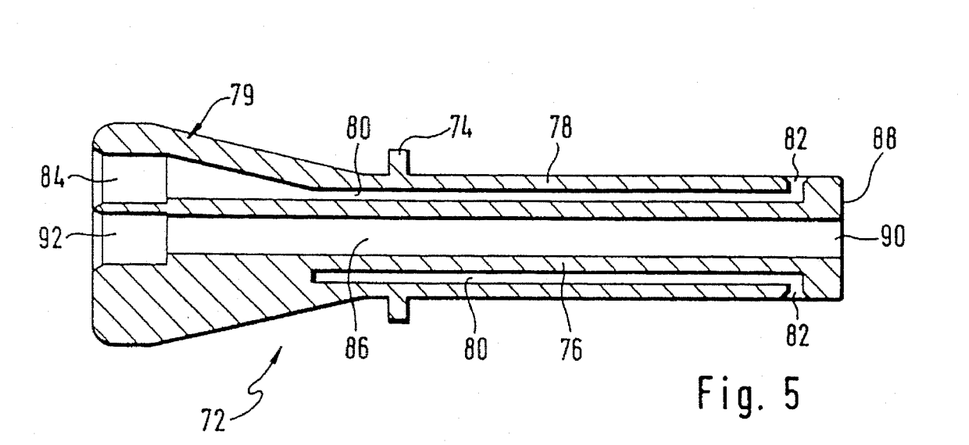
FIG. 5 is a schematic side view of a bicarbonate bag plug, similar to the plug depicted in FIG. 2.

A central channel 86, which leaves the front end 88 through the opening 90, which end faces the socket body 12, passes through the inner tube 76 and opens into the opening 92 in the handle section 79.

In the connected state, as depicted in FIG. 2, water can flow out of the duct 44 through the opening 82' the channel 80, and the channel 96, into the bag 100 and there dissolves the bicarbonate. Because of the sealed bag 100 the bicarbonate solution flows through the filter 102 and the channel 98 back into the plug 20 from which it flows into the outlet channel 42. This results in a circuit through the connector arrangement according to the invention, which results in a mixing of water and bicarbonate and thus to the preparation of a bicarbonate concentrate.

The front end 88' which surrounds the opening 90 in the shape of a ring, is—as can be seen in particular in FIGS. 1 and 2—engaged with a plurality of projections 108, which are disposed in a circle on the valve element 50'. Fluid can thus flow into the left chamber half 38 between the projections 108 past the valve element 50' when the plug is coupled.

FIG. 2 further shows that the plug 20 in the connected state is in a flow connection with the inlet channel 44 via the opening 82' such that on both sides of the opening 82', the two ring-shaped sealing arrangements 46 and 48 seal against the outer tube 78'. On the other side, the front opening 90' of the plug 20 lies on the far side of the innermost ring-shaped sealing arrangement 48 on the side of the left chamber half 38 and can thus not be brought directly into a flow connection with the opening 82' (only via the bag 100).

FIG. 2 also shows schematically that the magnet 64 in the coupling state activates the reed switch 66 and thus the sensor 68, such that the operationally ready installed position of the plug 20 can be verified.

Figure 3:
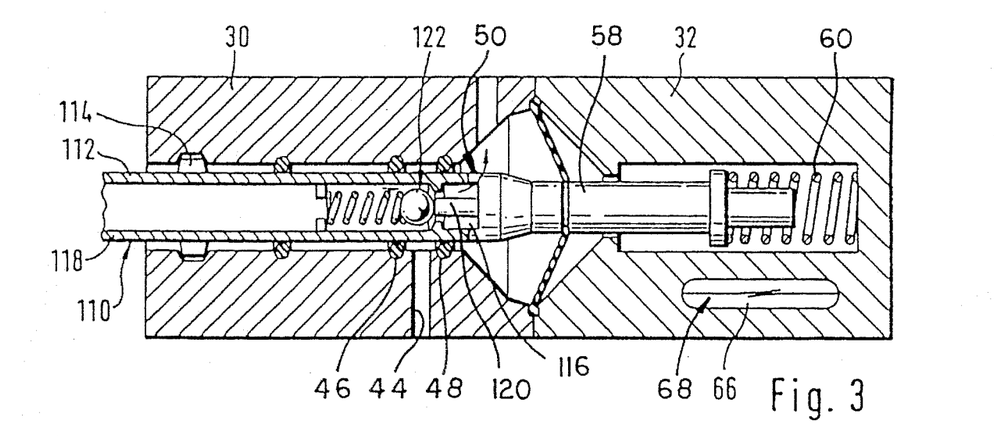
FIG. 3 is a view, similar to FIGS. 1 and 2, wherein a plug is connected to the connector of a central concentrate supply.

FIG. 3 depicts an operating state in which a plug component 110 is inserted into the coupling socket 10. This plug component 110 consists of only a tube 112 and likewise has a catch element 114 which engages the catch groove 18. The plug component 110 is dimensioned such that it extends even beyond the innermost ring-shaped sealing arrangement 48 in the snapped-in state and likewise works with the projections 108 of the valve element 50 and thus shifts the valve element 50 backward against the spring 60. Thus, the front opening 116 of the opener is likewise in a flow connection with the outlet channel 42. The other end 118 can be linked via a hose or tube (not shown) with a concentrate unit. In this case, the water source is blocked (through blockage of the inlet channel 44).

FIG. 3 further shows that a central projection 120 protruding axially forward is provided on the valve element 50, which projection extends in the coupled state into the opening 116, without completely sealing it, and there opens a check-valve 122 provided in the tube 112.

Also in FIG. 3 the sensor arrangement 68 is activated in the same manner as in the operating state according to FIG. 2 such that the operationally ready installation of the plug component 110 is signaled after complete coupling and locking.

Figure 6:
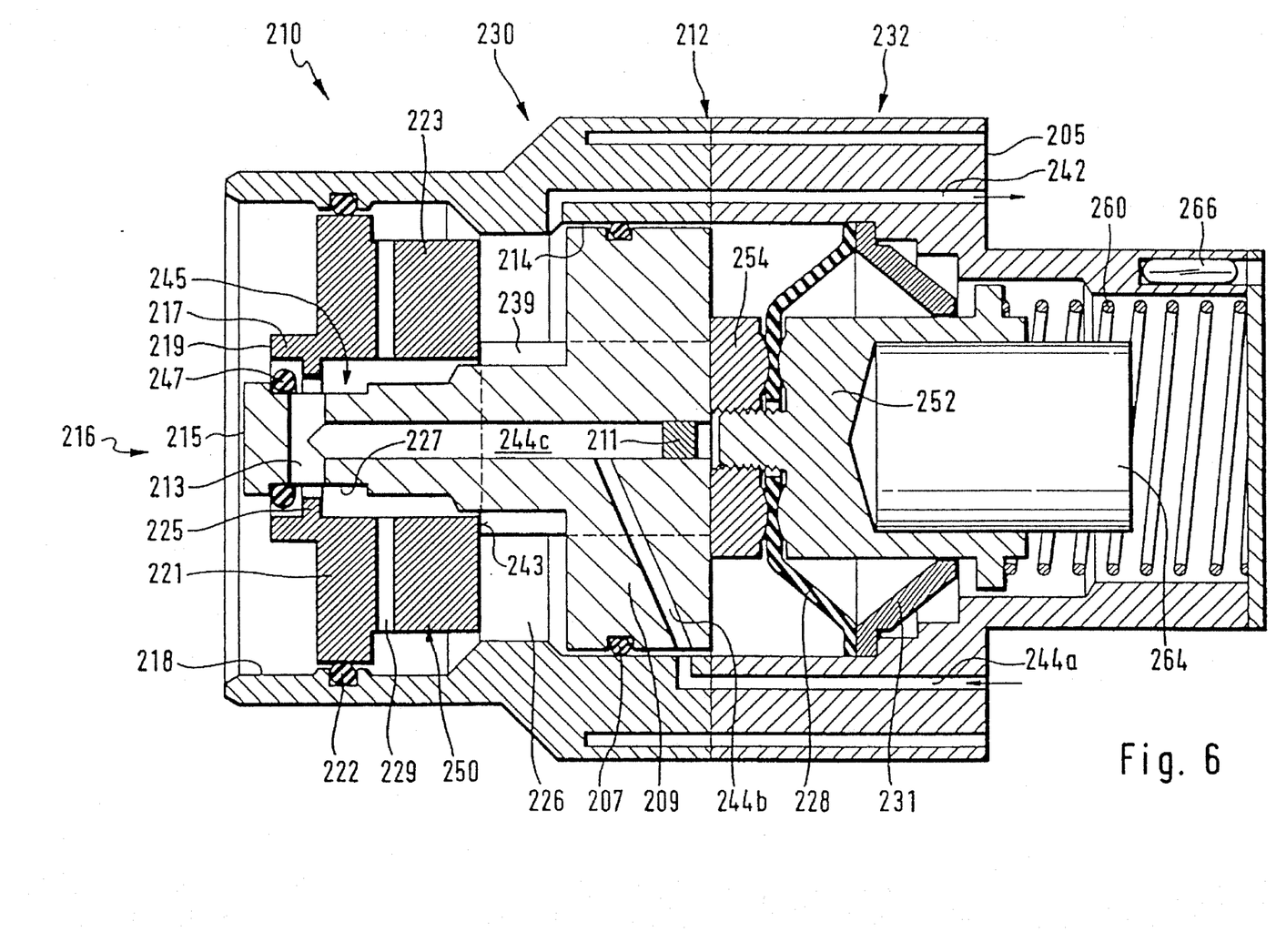
FIG. 6 illustrates an embodiment of the second plug component in the closed position in longitudinal section.
Figure 7:
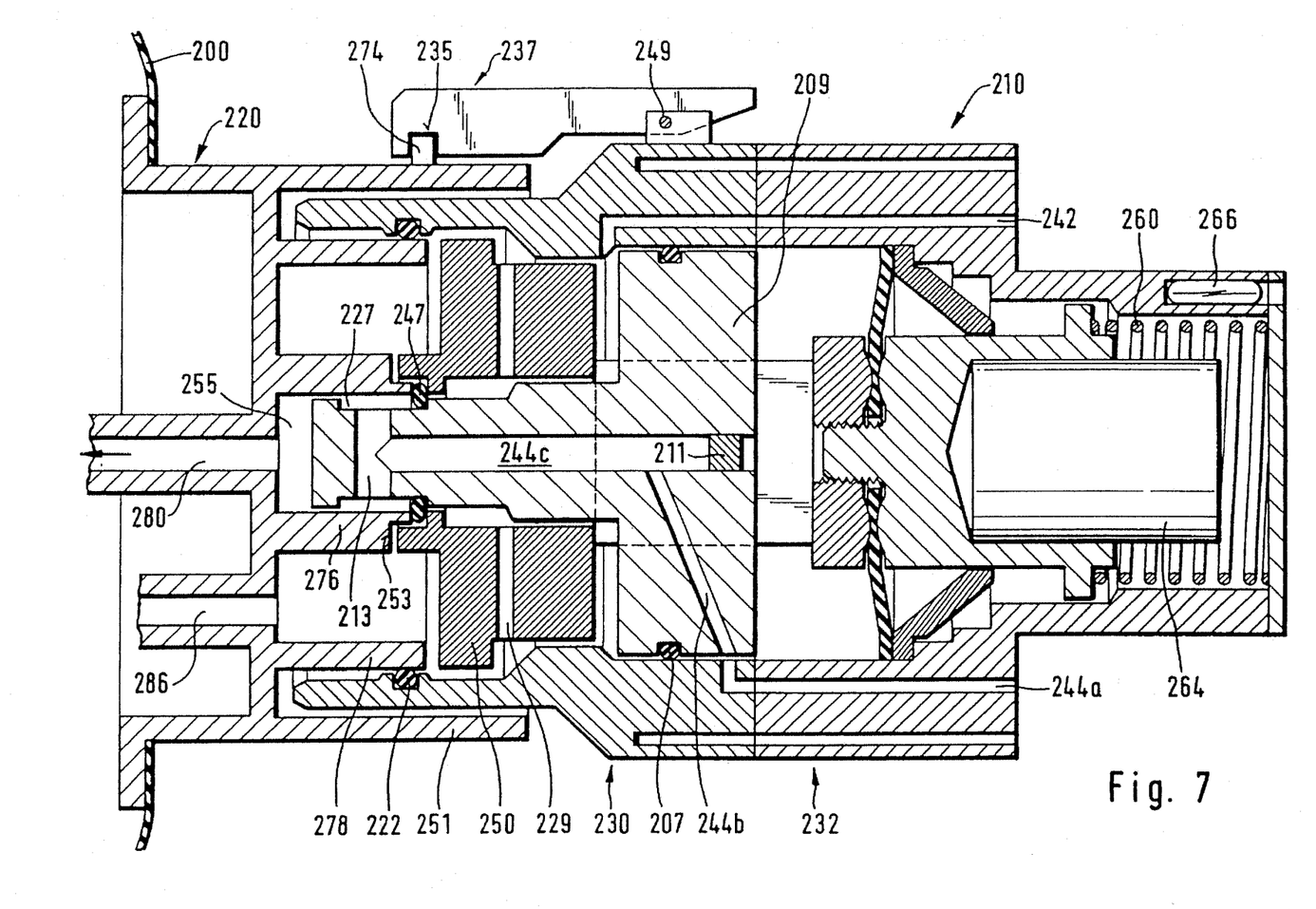
FIG. 7 illustrates an embodiment of the second plug component with the first plug component with a bag attached, likewise in longitudinal section.
Figure 8:
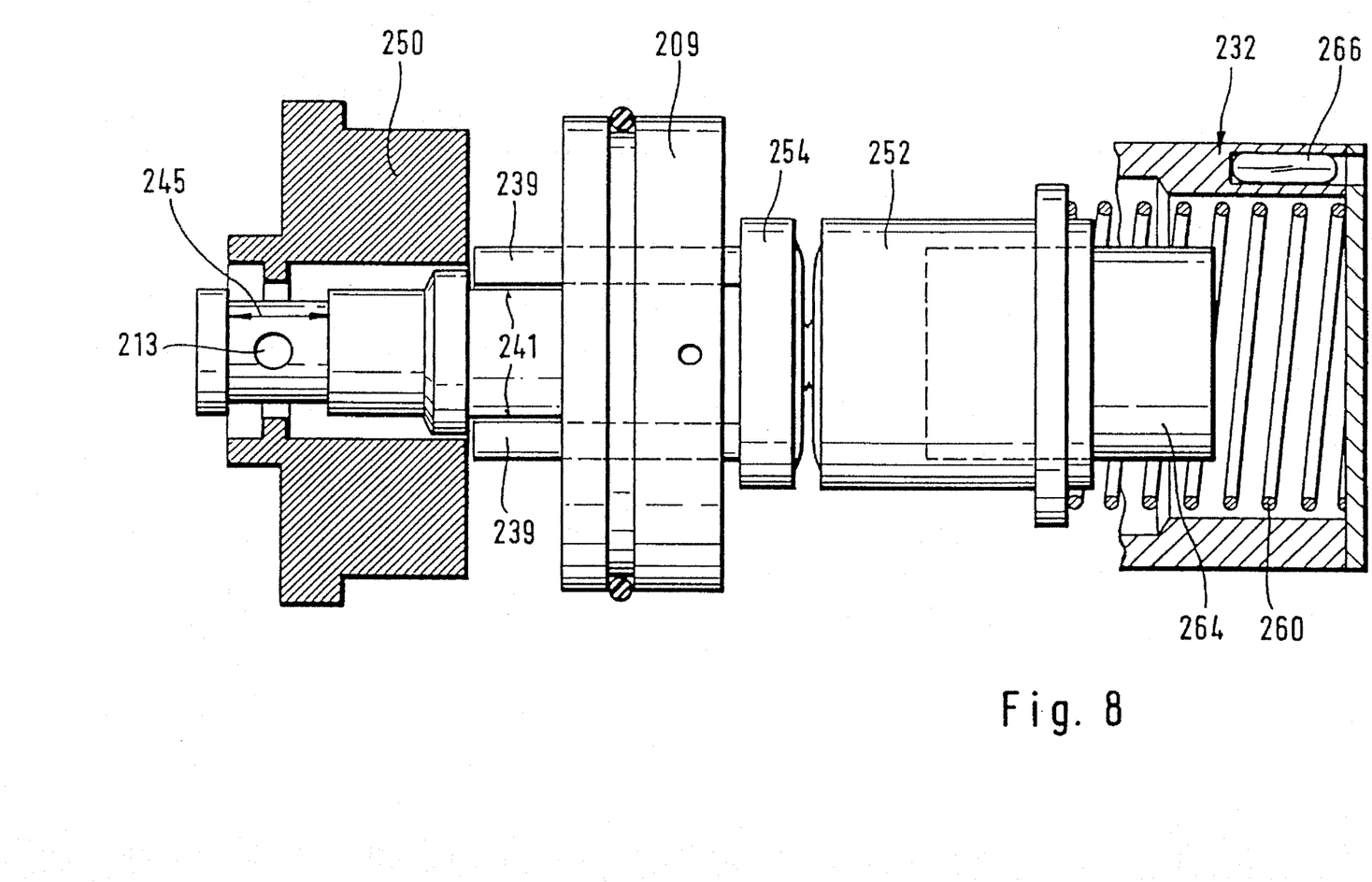
FIG. 8 illustrates the moving elements of the second plug component depicted in FIGS. 6 and 7 in longitudinal section (rotated 90° relative to FIG. 7.

According to another exemplary embodiment of the invention, depicted in FIGS. 6 through 8, a flexible bag with bicarbonate powder is claimed to be connectable to the second plug component by means of an appropriate first plug component, whereby fluid is fed to the bag and bicarbonate removed from it via the plug connector. The structure of the socket body and the valve chamber, in particular the right half of the valve chamber with the control elements is similar to the above described embodiment of the invention. Consequently, in the following basically the differences in the first plug component as well as the input part of the second plug component from the embodiments according to FIG. 1 through FIG. 5 are described.

The input part 230 of the socket body 212 faces the first plug component 220 of the bicarbonate bag 200 which is to be attached. This side is referred to in the following as the input side 216. The output part 232 of the socket body 212 connects on one side to the input part 230 of the socket body; the channels 244a and 242 open into the opposing face 205, referred to in the following as the output side.

In the input part 230, a sealing liner 209 and a valve liner 250 are installed. The sealing liner is stationarily fitted. It has a central bore 244c extending longitudinally as a continuation of the flow-in channel 244a, b. From the central bore 244c, a connecting channel 244b extends to the channel section 244a, whereby the channel section 244a is incorporated into the wall of the socket body 212. Thus, a complete fluid connection is made from the face 205 all the way to the central bore 244c of the sealing liner 209. The section of the central bore 244c between the channel section 244b and the end of the sealing liner 209 is sealed by a sealing stopper 211. The end of the central bore facing the input side opens into a transverse bore 213, which extends parallel to the input side 216. The face 215 ends the sealing liner 209 on the input side.

The sealing liner 209 is shaped on its end facing the output side 205 such that it fits sealingly into the bore 214. For sure sealing an O-ring 207 is inserted between the lining and the lining body in the socket body 212. Between the outlet of the channel 242 for the fluid discharge into the bore 214 and the input side 216 the diameter of the sealing liner 209 is significantly reduced. The intermediate space created in the valve chamber 226 between the sealing liner and the input part 230 of the socket body is partially sealingly filled by the movably disposed valve element, a cylindric valve sleeve 250.

The valve sleeve 250 likewise has sections with different diameters. A first ring-shaped section 217 extends from the input side into the bore 14. This section has a significantly smaller diameter than the bore 214. The face of the section 217 facing the input side serves as the stop surface 219 for the bag-side plug component. The first ring-shaped section 217 is followed on the side away from the stop surface 219 by a ring-shaped section 221, which is inserted sealingly into the bore 214. An O-ring 222 inserted into the socket body between this section 221 and the socket body 230 seals the device-side plug component 210 securely against the outside. A third ring-shaped section 223 forms the end of the valve lining 250 directed toward the output part 232. The diameter of this section 223 is selected such that it fits with clearance into a corresponding narrowing of the bore 214. In contrast to the embodiment described in FIGS. 1 to 4, the valve element 250 is not designed here as one piece to rest against the spring. Here the force of the spring is instead transmitted to the valve element 50 via a magnetic liner 252 and a stopper 254. The valve liner 250 seats with adequate play on the sealing liner 209, such that it can be shifted without difficulty, and also such that adequate space remains for the passage of the fluid. Only in the region of the first and/or the second ring-shaped section 217, 221, respectively, of the valve liner 250 does a thickening 225 of the valve liner 250 extend in close fit with the sealing liner 209. In the region of the thickening 225, the sealing liner 209 has a recess 227, in which a movable O-ring 247 is disposed, which O-ring is guided in the recess 227 by the thickening 225. The transverse bore 213 opens in the region of the recess 227. The region 245, in which the valve element 250 is movable extends, so far that in the closed position a secure seal of the second plug part against the outside is assured, and that when a bag is attached, the flow paths of the feed or discharge of fluid are safely separated. The valve liner 250 has in the third ring-shaped section 223 a radial bore 229 running parallel to the input side.

By shifting the valve liner 250, the control components disposed in the output part 232 of the socket body are activated. The shifting is effected either by connection of the bicarbonate bag or by attachment of a locking cap (not shown) in which the two flow paths (feed and discharge) are short-circuited. The locking cap is attached to enable complete sterilization of the second plug component 212.

By insertion of the sealing liner 209 into the valve chamber, the movable valve element 250 is linked not as one piece with the control components of the right valve chamber half. The activation now occurs via the stopper 254 linked with the now magnetic liner 252. The stopper is screwed to the magnetic liner, and in the region of the screwing, the elastic wall 228 is simultaneously locked in the center of the bore 214. In the region of the screwing to the magnetic liner 252, the stopper 254 has the same external diameter as the liner. A second section of the stopper with a smaller diameter extends, as is seen in particular in FIG. 8, out of the section 232 of the socket body into the input section 230. This second section of the stopper 254 consists of two circular arc segments, which extend as fork arms 239 through appropriate recesses in the sealing liner 209. The fork arms 239 are guided into the recesses 241 of the sealing liner, but the fork arms extend beyond the diameter of the sealing liner 209. They overlap in the region of a stop surface 243 with the surfaces of the valve liner 250 facing the output side 205. The shifting movement is transmitted via the stop surface 243 from the valve liner 250 to the magnet 264.

In the following, the mode of operation of the second plug component 210 in the closed position (without bag) and with a bicarbonate bag attached or a sealing cap applied are explained.

FIG. 6 depicts the second plug component 210 according to the invention without a bicarbonate bag attached and without the locking cap attached for sterilization of the second plug component. In this position the preloaded compression spring 260 presses the magnetic liner 252 against the guide liner 231. Since the stopper 254 is rigidly linked with the magnetic liner 252, in this position it experiences maximum travel into the input part 230 of the socket body. Thus, the valve liner 250 is also pushed by the stop surface 243 maximally toward the input side. In this position, the O-ring 247 is locked between the thickening 225 of the valve liner 250 and the input-side boundary of the recess 227 of the sealing liner 209. The passage of the fluid between the sealing liner 209 and the valve liner 250 is thus effectively sealed against the outside. Simultaneously, the second section 221 of the valve liner 250 rests sealingly against the O-ring 222 inserted in the socket body 230. Thus, passage of fluid between the valve liner 250 and the socket body 230 is also impossible.

In this position, the second plug component 210 can be rinsed. As indicated by the direction of the arrow at the entrance of the fluid intake channel 244a, water or disinfectant solution flows through the channel 244 into the central bore 244c and from there the fluid goes via the transverse bore 213 into the space between the sealing liner and the valve liner, since the other end of the central bore 244c is sealed by the sealing stopper 211. Through the radial bore 229, the fluid likewise arrives into the space between the valve liner and the socket body. This assures that no dead spaces develop and that the second plug component 210 is completely flushed. The water or the disinfectant solution is then eliminated through the channel 242 for the fluid discharge.

FIG. 7 shows the position of the movable elements of the second plug component when a bicarbonate bag is mounted on the input side of the coupling socket. The plug 220 is linked without intermediate tubing directly with the bicarbonate bag 200. The second plug component 210 and plug 220 are solidly linked to each other by a notched latch 237. The notched latch 237 is attached movably via a pivot 249 on the coupling socket and, by means of a notch 235, engages a locking projection 274 of the plug 220. On the side away from the bicarbonate bag 200, the plug 220 has three concentric ring walls. The first, outer ring wall 251 bears the locking projection 274 and surrounds a section of the socket body 230. This outer ring wall 251 is the ring wall which protrudes the farthest.

The ring wall 278 set back relative to the outer ring wall engages sealingly with the ring seal 222 inserted into the socket body 230. The inner ring wall 276 is set back still farther relative to the center ring wall 278. When the plug is in the inserted position, the face 253 of the inner ring wall facing the plug component 210 rests against the face of the valve liner 250 facing the input side. Thus, upon insertion of the plug 220, as a result of the contact of the face 253 against the valve liner 250, the latter is moved against the pressure of the spring 260 to the output side of the second plug component 210. When the plug 220 is locked on the second plug component 210 by the locking projection 274, the ring seal 247 is also moved, by the shifting of the valve liner 250 effected by the face 253 of the inner ring wall, from the input-side boundary of the recess 227 to the opposite, output-side boundary of the recess 227. Thus, the water flowing via the feed channel 244a into the central bore 244c flows via the transverse bore 213 out of the second plug component 210 into the intermediate space surrounded by the inner ring wall 276 which is sealed by the O-ring 247 against the second plug component 210, and which is provided with an outlet 280, though which the water leaving the transverse bore 213 can flow out into the interior of the bag 200. The concentrated bicarbonate solution produced in the bag 200 is sucked out via an input line 286, which is provided on its entry end with a filter (not shown). The input line 286 opens into the circular intermediate space between the inner ring wall 276 and the center ring wall 278. Mixing of the bicarbonate solution with the incoming water is impossible since communication between the two cavities is blocked by the ring seal 247. The incoming bicarbonate solution moves out of the cavity between the inner and the center ring wall into the intermediate space between the valve liner 250 and the socket body 230. It is further conducted through the radial bore 229 into the space between the sealing liner 209 and the valve liner 250, to be eliminated through the channel 242 to the bicarbonate solution discharge line. It is advantageous to dispose the channel 242 above the feed channel 244, thus assuring that any $CO_2$ generated is safely discharged along with the bicarbonate solution. Escape of the bicarbonate solution from the second plug component 210 is prevented in that the center ring wall 278 is sealingly engaged with the ring seal 222. The second embodiment of the invention described here enables a particularly secure plug connection and guarantees a simple and certain separation of the two flow paths from each other via this connection.

By the shifting of the magnet 264, i.e., by the attachment of a bag, a reed switch 266 with appropriate control devices (not shown) is again activated.

If, for cleaning or sterilization of the second plug component 210 a locking cap is placed on the input side of the socket body 230, this locking cap is constructed the same as the plug 220, with the difference that the lines 280 and 286 respectively do not open into a bag 200, but are short-circuited instead. Consequently, the water or the disinfectant solution flows out of the transverse bore 213 via the short-circuited line directly into the intermediate space between the inner ring wall 276 and the center ring wall 278 and back through the spaces between the socket body 230, the valve liner 250, and the sealing liner 209 to the discharge channel 242. Thus, all surfaces which come into contact with the bicarbonate solution are completely and thoroughly cleaned or disinfected.

Figure 9:
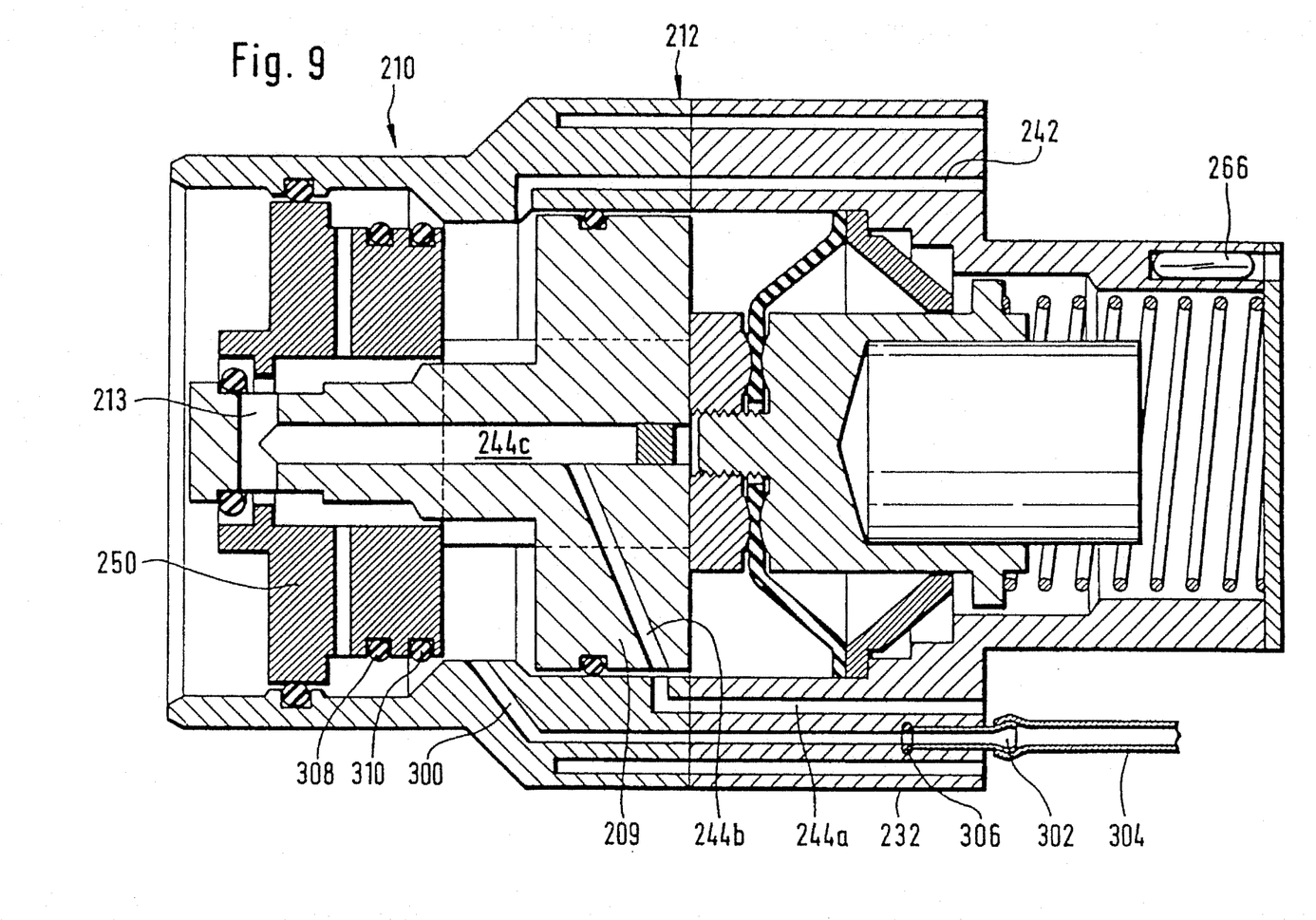
FIG. 9 illustrates another embodiment of the second plug component in longitudinal section.
Figure 10:
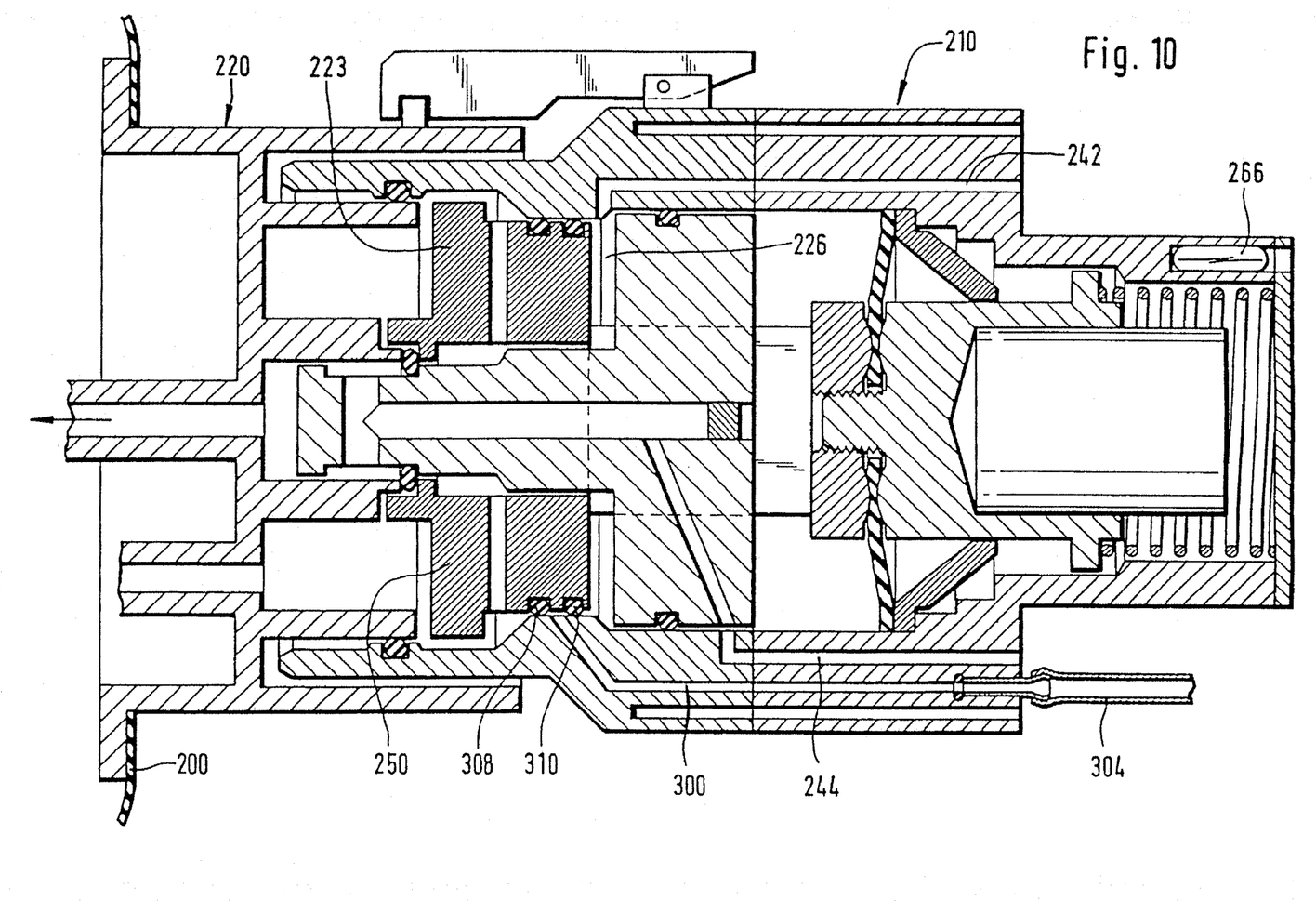
FIG. 10 illustrates the embodiment of the second plug component as in FIG. 9, but with a bag attached.

An additional embodiment of the plug connector according to the invention is depicted in FIGS. 9 and 10. This embodiment takes into account the fact that not only are fluid concentrates prepared from solids with the arrangement according to the invention, but also that by means of one and the same arrangement liquid concentrates can be diluted or, if appropriate, a plurality of concentrates or dialysis fluid concentrates can be prepared. For that purpose, the second plug component 210 has an additional channel 300 in the socket body for the addition of fluid concentrate. The channel leads from the output side of the socket body 232 to the cavity between the sealing liner 209 and the valve liner 250, as shown in FIGS. 9 and 10. A tube 304 is connected to the channel 300 via a spout 302 inserted in the channel 300. The spout 302 is sealed by an O-ring 306 against the socket body 232. The tube 304 is linked at its other end either with a concentrate container, e.g., for highly concentrated bicarbonate solution, or, during rinsing of the device, with the dialysis fluid circuit. In the position of the second plug component 210 depicted in FIG. 9, concentrate is delivered from the container with the highly concentrated bicarbonate solution into the cavity between the sealing liner 209 and the valve liner 250. As appropriate, dilution water likewise flows into the cavity between the sealing liner 209 and the valve liner 250 via the channel 244 as well as the transverse bore 213. By means of control devices (not shown), it is assured that a predefined mix ratio is maintained. The diluted fluid is then forwarded via the channel 242 out of the second plug component 210 to the dialysis device.

When the first plug component 220 is mounted, the concentrate channel 300 is sealed against the valve chamber 226 by O-rings 308, 310, which are disposed on the valve element 250, advantageously on the third circular section 223. The O-rings 308, 310 are disposed on the third circular section 223 such that they rest on both sides of the opening of the concentrate channel 300 when the bag 200 is in place.

With this mode of use of the second plug component 210, the cleaning or sterilization of the coupling socket is performed in that the other end of the tube 304 is removed from the canister with the highly concentrated fluid solution and is connected to the dialysis device such that water or disinfectant solution flows through both the feed channel 244 and through the concentrate channel 300 into the second plug component, flushes it thoroughly, and then is discharged out the channel 242.

According to a preferred embodiment of the invention, corresponding marks (not shown) can be provided on the outside of the central ring wall 28 and on the inner surface of the second plug component for identification of different concentrate bags. These marks could, for example, comprise groove and spring arrangements or mating rings. They guarantee that only bags with predetermined concentrates can be coupled to the connector and tube connections provided for them.

What is claimed is:

1. A bag for use in apparatus for dialysis to accommodate solid or fluid concentrate for preparation of dialysis fluid using a dialysis machine, the bag having a bag body and at least one opening, wherein a first plug component is provided on the opening of the bag, which first plug component is an elongate tube extending from a first end to a second end and which sealingly surrounds the opening at said second end, whereby in a coupled state the first plug component produces a flow connection with the bag, the first plug component including coupling means at said first end, which are connectable with a second complementary plug component provided on the dialysis machine, creating a first flow path from the dialysis reaching to the bag and a second flow path back from the bag to the dialysis machine, wherein the first plug component having an inlet for fluid flowing from the dialysis machine to the bag, and an outlet for diluted concentrate going back from the bag to the dialysis machine located at said first end adjacent said coupling means.

2. The bag according to claim 1, characterized in that said tube is projecting into the interior of the bag.

3. The bag according to claim 2, characterized in that the second end of the tube is provided on its free end with a filter.

4. The bag according to claim 1, characterized in that the first and the second flow paths are disposed concentrically.

5. The bag according to claim 4, characterized in that the first and the second flow paths open respectively into an inlet and an outlet, which are likewise disposed concentrically.

6. The bag according to claim 4, characterized in that the first and the second flow paths open respectively into an inlet and an outlet, which are disposed in parallel.

7. The bag according to claim 1, characterized in that the first and the second flow paths are disposed in parallel.

8. The bag according to claim 1, characterized in that the plug component has coding which characterizes specific bag contents in each case.

9. The bag according to claim 1, characterized in that the plug component has catch means which assure the leak-proof connection with the second plug component.

10. A plug connector for use with a bag to accommodate solid or fluid concentrate for the preparation of dialysis fluid using a dialysis machine, having two plug components, whose first plug component is attached on the opening of the bag, and whose second plug component is disposed on the dialysis machine and is connected to a dialysis fluid feed line, wherein the second plug component consists of a socket body, in which an essentially cylindric recess open to the surroundings is designed, into which the first plug component can be inserted, and in which, in a valve chamber, a valve element is shiftably disposed, the valve chamber is linked to an outlet channel, and an inlet channel opens into a region of the recess, in which the valve element is shiftable, the valve element being shiftable toward the input side of the second plug component in a forward position, in which the inlet channel and the outlet channel are in fluid communication with each other and in which the inlet channel and the outlet channel are not in fluid communication with the input side of the second plug component, and the valve element being shiftable away from the input side in a backward position, in which the inlet channel and the outlet channel are in fluid communication with the input side of the second plug component and the valve element is preloaded by means of an elastic element in the forward position.

11. The plug connector according to claim 10, characterized in that a sealing liner is inserted in the valve chamber through which the inlet channel is guided such that it opens into the region, in which the valve element is shiftable.

12. The plug connector according to claim 11, characterized in that the sealing liner is sealed against the socket body with at least one O-ring.

13. The plug connector according to claim 10, characterized in that sealing means are provided in the valve chamber, in the region of the recess in which the valve element is shiftable or both.

14. The plug connector according to claim 13, characterized in that the sealing means comprise a movable O-ring which is disposed depending on the position of the valve element respectively sealingly alternatively between the inlet channel and the outlet channel, or seals the valve chamber between the valve element and the sealing liner against the input side of the second plug component.

15. The plug connector according to claim 13, characterized in that the sealing means further comprise an O-ring, which seals the valve chamber between the socket body and the valve element in the closed position against the input side of the second plug component.

16. The plug connector according to claim 13, characterized in that the sealing means comprise two O-rings placed at an interval from each other in the recess or disposed on the sealing liner, between which O-rings the inlet channel opens, and can respectively be engaged alternatively with the valve element.

17. The plug connector according to claim 10, characterized in that the valve element is provided on its side region facing the valve chamber with a smaller diameter.

18. The plug connector according to claim 17, characterized in that the valve element has a radial boring on its side region facing the valve chamber.

19. The plug connector according to claim 10, characterized in that the valve element is provided on the side facing the recess or the input side with valve activation means.

20. The plug connector according to claim 10, characterized in that the valve chamber is partitioned off from the elastic element by means of an elastic wall.

21. The plug connector according to claim 10, characterized in that in the recess at least one seal is disposed to seal the first plug component when the two plug components are coupled with each other.

22. The plug connector according to claim 10, characterized by a sensor means to determine the position of the valve element.

23. The plug connector according to claim 10, characterized by catch means to lock the first plug component in the recess.

24. The plug connector according to claim 10, characterized in that for the cleaning of the second plug component a complementary cap is attached to its input side, which cap moves the valve element out of the closed position, and by means of which the first and second flow path are short-circuited.

25. The plug connector according to claim 10, characterized in that the second plug component has codes which correspond in each case with codes on the first plug component.

26. The plug connector according to claim 10, characterized in that a second inlet channel opens into the valve chamber, which channel, depending on the operating state, is linked either with an additional concentrate container or with the dialysis fluid circuit.

27. The plug connector according to claim 26, characterized in that the second inlet channel is sealed against the valve chamber by sealing means installed on the valve element, when the first and the second plug components are coupled with each other.

28. The plug connector according to claim 10, characterized in that the valve element can be brought into a first position, in which the valve chamber is sealed against the input side of the recess, but is linked with at least one inlet channel and the outlet channel, and into a second position in which the inlet channel is linked with the recess and the valve chamber with the outlet channel, and a channel of the first plug component opens into the valve chamber.

29. The plug connector according to claim 10, characterized in that the valve element can be brought into a position in which the inlet channel is locked, and one channel of a plug in the form of a tube opens into the valve chamber linked with the outlet channel.

30. Apparatus for dialysis, comprising:

a dialysis machine having a dialysis fluid feed line;

a bag to accommodate solid or fluid concentrate for preparation of dialysis fluid, said bag including a bag body and at least one opening;

a first plug component provided on the opening, which plug sealingly surrounds the opening, the first plug component having an inlet for fluid flowing out of the dialysis machine and an outlet for diluted concentrate flowing back to the dialysis machine;

a second plug component disposed on the dialysis machine and connected to the dialysis fluid feed line, the second plug component comprising a socket body in which an essentially cylindrical recess open to its environment is provided into which the first plug component is insertable and in which a valve element preloaded in a closed position by means of an elastic element is shiftably disposed in a valve chamber, the valve chamber being linked to an outlet channel and an inlet channel opening into a region of the recess in which the valve element is shiftable; and detachable means for coupling the first and second plug components, whereby when the first and second plug components are connected a first flow path from the dialysis machine to the bag and a second flow path back from the bag to the dialysis machine are formed.

31. Apparatus according to claim 30, wherein the inlet of the first plug component for fluid of the dialysis machine and the outlet plug component for diluted concentrate flowing back to the dialysis machine are respectively linked with a tube projecting into the bag.

32. Apparatus according to claim 31, wherein the tube linked to the outlet is provided at a free end thereof with a filter.

33. Apparatus according to claim 30, wherein a sealing liner is inserted in the valve chamber through which the inlet channel is guided such that it opens into the region in which the valve element is shiftable.

34. Apparatus according to claim 33, wherein the sealing liner is sealed against the socket body with at least one O-ring.

35. Apparatus according to claim 30, wherein sealing means are provided in at least one of the valve chamber and the region of the recess in which the valve element is shiftable.

* * * * *